US00PP28126P3

(12) United States Plant Patent
Koekkoek

(10) Patent No.: US PP28,126 P3
(45) Date of Patent: Jun. 20, 2017

(54) ***ALSTROEMERIA* PLANT NAMED 'TESINDIG IMP'**

(50) Latin Name: *Alstroemeria hybrida*
Varietal Denomination: TESINDIG imp.

(71) Applicant: Arthur N. J. Koekkoek, Alkmaar (NL)

(72) Inventor: Arthur N. J. Koekkoek, Alkmaar (NL)

(73) Assignee: Vof Hortipartners, Heerhugowaard (NL)

( * ) Notice: Subject to any disclaimer, the term of this patent is extended or adjusted under 35 U.S.C. 154(b) by 44 days.

(21) Appl. No.: 14/756,653

(22) Filed: Sep. 29, 2015

(65) Prior Publication Data

US 2017/0094865 P1 Mar. 30, 2017

(51) Int. Cl.
*A01H 5/02* (2006.01)

(52) U.S. Cl.
USPC ..... Plt./309

(58) Field of Classification Search
USPC ..... Plt./309
See application file for complete search history.

*Primary Examiner* — Keith Robinson
(74) *Attorney, Agent, or Firm* — C. A. Whealy

(57) ABSTRACT

A new and distinct cultivar of *Alstroemeria* plant named 'Tesindig imp.', characterized by its broadly upright plant habit; relatively short flowering stems; sturdy and strong plants; moderately vigorous growth habit; numerous large purple-colored flowers; and good garden performance.

1 Drawing Sheet

Botanical designation: *Alstroemeria hybrida.*
Cultivar denomination: 'TESINDIG imp.'.

BACKGROUND OF THE INVENTION

The present invention relates to a new and distinct cultivar of *Alstroemeria* plant, botanically known as *Alstroemeria hybrida*, grown typically as a potted garden *Alstroemeria*, and hereinafter referred to by the name 'Tesindig imp.'.

The new *Alstroemeria* plant is a product of a planned breeding program conducted by the Inventor in Heerhugowaard, The Netherlands. The objective of the breeding program is to create new potted garden *Alstroemeria* plants with numerous attractive flowers and flower continuously during the flowering season.

The new *Alstroemeria* plant is a naturally-occurring whole plant mutation of *Alstroemeria hybrida* 'Tesindig', not patented. The new *Alstroemeria* plant was discovered and selected by the Inventor as a single flowering plant from within a population of plants of 'Tesindig' in a controlled greenhouse environment in Heerhugowaard, The Netherlands in June, 2013.

Asexual reproduction of the new *Alstroemeria* plant by root divisions in a controlled greenhouse environment in Heerhugowaard, The Netherlands since September, 2013 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Tesindig imp.'. These characteristics in combination distinguish 'Tesindig imp.' as a new and distinct *Alstroemeria* plant:

1. Broadly upright plant habit; relatively short flowering stems.
2. Sturdy and strong plants; moderately vigorous growth habit.
3. Numerous large purple-colored flowers.
4. Good garden performance.

Plants of the new *Alstroemeria* can be compared to plants of the mutation parent, 'Tesindig'. Plants of the new *Alstroemeria* differ from plants of 'Tesindig' in the following characteristics:

1. Plants of the new *Alstroemeria* are larger and more vigorous than plants of 'Tesindig'.
2. Plants of the new *Alstroemeria* have larger leaves than plants of 'Tesindig'.
3. Plants of the new *Alstroemeria* have larger flowers than plants of 'Tesindig'.

Plants of the new *Alstroemeria* can be compared to plants of the *Alstroemeria hybrida* 'Tesmach', disclosed in U.S. Plant Pat. No. 22,266. In side-by-side comparisons, plants of the new *Alstroemeria* differ primarily from plants of 'Tesmach' in flower color as plants of 'Tesmach' had red purple-colored flowers. Additionally, flowers of the new *Alstroemeria* had more stripes than flowers of 'Tesmach'.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant.

The photograph comprises a side perspective view of typical flowering plants of 'Tesindig imp.' grown in a container.

DETAILED BOTANICAL DESCRIPTION

Plants used for the aforementioned photograph and following observations and measurements were grown during the winter and early spring in 24-cm containers in a glass-covered greenhouse in Kudelstaart, The Netherlands. During the production of the plants, day temperatures ranged from 12° C. to 15° C. and night temperatures averaged 12° C. Plants used in the photograph were 15 weeks old and plants used for the description were 22 weeks old. Color references are made to The Royal Horticultural Society Colour Chart, 2007 Edition, except where general terms of ordinary dictionary significance are used.

Botanical classification: *Alstroemeria hybrida* 'Tesindig imp.'.

Parentage: Naturally-occurring whole plant mutation of *Alstroemeria hybrida* 'Tesindig', not patented.

Propagation:

*Type*.—By root divisions.

*Time to produce a rooted young plant, summer*.—About seven weeks at temperatures about 20° C.

*Time to produce a rooted young plant, winter*.—About eight weeks at temperatures about 16° C.

*Root description*.—Fibrous and fleshy; thick to thin; typically white in color, actual color of the roots is dependent on substrate composition, water quality, fertilizer type and formulation, substrate temperature and physiological age of roots.

*Rooting habit*.—Freely branching; medium density.

*Rhizome length*.—About 12.3 cm.

*Rhizome diameter*.—About 3 mm.

*Rhizome texture*.—Smooth, glabrous.

*Rhizome luster*.—Slightly glossy.

*Rhizome color*.—Close to 8D.

Plant description:

*Plant and growth habit*.—Herbaceous perennial; broadly upright plant habit with relatively short flowering stems, flattened globular; freely branching habit with about 21 primary lateral branches developing per plant; sturdy and strong plants; moderately vigorous growth habit.

*Plant height*.—About 20 cm.

*Plant diameter* (*area of spread*).—About 40.8 cm.

Lateral branch description:

*Aspect*.—Mostly upright to outwardly spreading.

*Length*.—About 13 cm.

*Diameter*.—About 8 mm.

*Internode length*.—About 7 mm.

*Strength*.—Moderately strong.

*Texture*.—Smooth, glabrous.

*Luster*.—Moderately glossy.

*Color*.—Close to 144A to 144B; with development, color becoming closer to 148A.

Leaf description:

*Arrangement*.—Alternate; below the peduncles in a single whorl; simple.

*Length*.—About 6.2 cm.

*Width*.—About 2.9 cm.

*Shape*.—Ovate to narrowly ovate and elliptic; twisting.

*Apex*.—Acute.

*Base*.—Cuneate.

*Margin*.—Entire.

*Texture, upper and lower surfaces*.—Smooth, glabrous.

*Luster, upper and lower surfaces*.—Matte.

*Venation pattern*.—Parallel.

*Color*.—Developing leaves, upper surface: Surface faces downwards; close to 137C to 137D. Developing leaves, lower surface: Surface faces upwards; close to between 141A and 143A. Fully expanded leaves, upper surface: Surface faces downwards; close to 137C; venation, close to 144A. Fully expanded leaves, lower surface: Surface faces upwards; close to N137A; venation, close to 144A.

*Petioles*.—Length: About 2.9 cm. Diameter: About 1 mm by 5 mm. Texture, upper and lower surfaces: Smooth, glabrous. Luster, upper and lower surfaces: Slightly glossy. Color: Close to 144A.

Flower description:

*Flower type and habit*.—Single zygomorphic flowers arranged in terminal umbels; flowers face mostly outwardly to slightly upright; perianth segments separate; freely flowering habit with about ten flowers per inflorescence and about 90 flowers developing per plant.

*Natural flowering season*.—Plants begin flowering about eight weeks after planting; flowering continuous from summer into the autumn in The Netherlands.

*Fragrance*.—None detected.

*Flower longevity on the plant*.—About ten days; flowers not persistent.

*Flower buds*.—Length: About 3.4 cm. Diameter: About 1.1 cm. Shape: Narrowly obovate. Color: Close to 145C and 149D; towards the apex, close to between N79B and 202A; towards the base, close to 143C.

*Umbel height*.—About 10.7 cm.

*Umbel diameter*.—About 15.2 cm.

*Flower diameter* (*horizontal*).—About 6.6 cm.

*Flower length* (*vertical*).—About 6.5 cm.

*Flower depth* (*height*).—About 6.8 cm.

*Perianth*.—Arrangement: Six arranged in two whorls, each whorl with two lateral and one median segments. Size, inner perianth: Length, lateral segments: About 6.8 cm. Width, lateral segments: About 2.4 cm. Length, median segment: About 5.6 cm. Width, median segment: About 2.4 cm. Size, outer perianth: Length, lateral segments: About 6.2 cm. Width, lateral segments: About 3.5 cm. Length, median segment: About 6.5 cm. Width, median segment: About 3.6 cm. Shape, inner perianth, lateral and median segments: Oblanceolate. Shape, outer perianth, lateral and median segments: Obovate. Apex, inner perianth, lateral and median segments: Abruptly acute. Apex, outer perianth, lateral and median segments: Emarginate. Base, inner perianth, lateral and median segments: Narrowly cuneate. Base, outer perianth, lateral and median segments: Long cuneate. Margin, inner perianth, lateral and median segments: Entire. Margin, outer perianth, lateral and median segments: Towards the apex, finely serrate; towards the base, entire. Texture, inner and outer perianths, lateral and median segments, upper and lower surfaces: Smooth, glabrous; slightly velvety. Luster, inner perianth, lateral and median segments, upper surface: Dull. Luster, inner perianth, lateral and median segments, lower surface: Slightly glossy. Luster, outer perianth, lateral and median segments, upper surface: Matte. Luster, inner perianth, lateral and median segments, lower surface: Moderately glossy. Color, inner perianth: When opening, lateral segments, upper surface: Distally, close to 77A; apex, close to N79B; proximally, close to NN155A; spots, close to N186C. When opening, median segment, upper surface: Close to 77A; apex, close to N79B; towards the base, close to N78B. When opening, lateral segments, lower surface: Distally, close to 77A; proximally, close to between 156C and 186D. When opening, median segment, lower surface: Close to 77A; apex, close to N79B; towards the base, close to N78B. Fully opened, lateral segments, upper surface: Distally, close to N81B; towards the apex, close to N79C; proximally, close to NN155C; spots, close to between N186C and 202A; color becoming closer to N82A to N82B with development. Fully opened, median segment, upper surface: Close to N81B; towards the apex, close to N81A; color becoming closer to N82A to N82B with development. Fully opened, lateral segments, lower surface: Distally, close to N81A to N81B; towards the apex, close to 77A; proximally, close to N81C. Fully opened, median segment, lower surface: Close to N80B; towards the apex, close to N80A. Color, outer perianth: When opening, lateral and median segments, upper surface: Close to 77A; apex, close to N79A to N79B; towards the base, close to 77B to 77C. When opening, lateral and median segments, lower surface: Close to 77A; center, close to N79B; apex, close to 203B. Fully opened, lateral and median segments, upper surface: Close to N82A; apex, close to N79A to N79B; towards the base, close to N81C; color becoming closer to N82B and towards the apex, close to N79B with development. Fully opened, lateral and median segments, lower surface: Close to N82A; apex, close to N79A to N79B; towards the base, close to N81C.

*Pedicels*.—Length: About 2.4 cm. Diameter: About 3.5 mm. Strength: Moderately strong. Angle: About 30° from stem axis. Texture: Smooth, glabrous. Color, upper and lower surfaces: Close to 146A.

*Reproductive organs*.—Stamens: Quantity per flower: Six. Filament length: About 3.7 cm. Filament color: Close to N80B; towards the base, close to 150D. Anther shape: Oblong. Anther length: About 8 mm. Anther color: Close to 197B. Pollen amount: Moderate. Pollen color: Close to 198A. Pistils: Quantity per flower: One. Pistil length: About 4.5 cm. Style length: About 4 cm. Style color: Close to N82B; towards the base, lighter than N82B. Stigma shape: Tri-parted; parts, club-shaped, curved. Stigma color: Close to N81A. Ovary color: Close to 138B with ribbing, close to N186A.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate high temperatures of about 35° C. and to be hardy to USDA Hardiness Zone 8.

It is claimed:

1. A new and distinct *Alstroemeria* plant named 'Tesindig imp.' as illustrated and described.

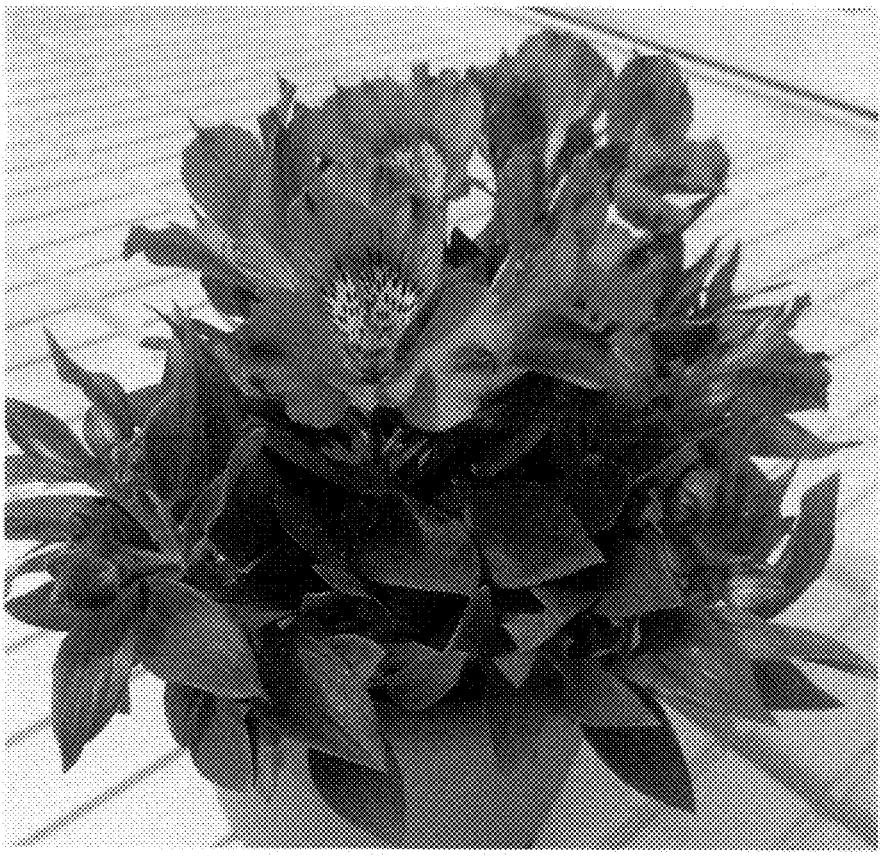

* * * * *